US012036006B2

(12) United States Patent
Gideon et al.

(10) Patent No.: US 12,036,006 B2
(45) Date of Patent: Jul. 16, 2024

(54) SYSTEM AND METHOD FOR TRAINING A REMOTE PHOTOPLETHYSMOGRAPHY MODEL

(71) Applicant: Toyota Research Institute, Inc., Los Altos, CA (US)

(72) Inventors: John H. Gideon, Howell, MI (US); Simon A. I. Stent, Cambridge, MA (US)

(73) Assignee: Toyota Research Institute, Inc., Los Altos, CA (US)

( * ) Notice: Subject to any disclaimer, the term of this patent is extended or adjusted under 35 U.S.C. 154(b) by 669 days.

(21) Appl. No.: 17/317,256

(22) Filed: May 11, 2021

(65) Prior Publication Data
US 2022/0296116 A1 Sep. 22, 2022

Related U.S. Application Data

(60) Provisional application No. 63/161,799, filed on Mar. 16, 2021.

(51) Int. Cl.
*A61B 5/024* (2006.01)
*A61B 5/00* (2006.01)
*G16H 50/50* (2018.01)

(52) U.S. Cl.
CPC ........ *A61B 5/02416* (2013.01); *A61B 5/7246* (2013.01); *A61B 5/7257* (2013.01); *A61B 5/7267* (2013.01); *A61B 5/743* (2013.01); *G16H 50/50* (2018.01); *A61B 2560/02* (2013.01)

(58) Field of Classification Search
CPC .............. A61B 5/02416; A61B 5/7246; A61B 5/7257; A61B 5/7267; A61B 5/743; A61B 2560/02; G16H 50/50; G16H 50/20; G16H 30/40
See application file for complete search history.

(56) References Cited

U.S. PATENT DOCUMENTS

2009/0226071 A1   9/2009   Schuler et al.

OTHER PUBLICATIONS

Yun-Yun Tsou, Yi-An Lee, Chiou-Ting Hsu, and Shang-Hung Chang. 2020. Siamese-rPPG network: remote photoplethysmography signal estimation from face videos. In Proceedings of the 35th Annual ACM Symposium on Applied Computing (SAC '20). Association for Computing Machinery, New York, NY, USA, 2066-2073. (Year: 2020).*
Hernandez-Ortega et al., "DeepFakesON-Phys: DeepFakes Detection based on Heart Rate Estimation," 8 pages, arXiv:2010.00400v3 [cs.CV] Dec. 14, 2020.
(Continued)

*Primary Examiner* — Patrick Fernandes
*Assistant Examiner* — Nicholas A Robinson
(74) *Attorney, Agent, or Firm* — Christopher G. Darrow; Darrow Mustafa PC

(57) ABSTRACT

Systems and methods for training remote photoplethysmography ("PPG") models that outputs a subject PPG signal based on a subject video clip of a subject are described herein. The system may have a processor and a memory in communication with the processor. The memory may include a training module having instructions that, when executed by the processor, cause the processor to train the remote PPG model in a self-supervised contrastive learning manner using an unlabeled video clip having a sequence of images of a face of a person.

17 Claims, 6 Drawing Sheets

(56) References Cited

OTHER PUBLICATIONS

Lee et al., "Meta-rPPG: Remote Heart Rate Estimation Using a Transductive Meta-Learner," 26 pages, arXiv:2007.06786v1 [cs.CV] Jul. 14, 2020.
Chen et al., "DeepPhys: Video-Based Physiological Measurement Using Convolutional Attention Networks," 16 pages, arXiv:1805.07888v2 [cs.CV] Aug. 7, 2018.
Niu et al., "Video-based Remote Physiological Measurement via Cross-verified Feature Disentangling," 16 pages, arXiv:2007.08213v1 [cs.CV] Jul. 16, 2020.
Yu et al., "Remote Photoplethysmograph Signal Measurement from Facial Videos Using Spatio-Temporal Networks," 12 pages, arXiv:1905.02419v2 [cs.CV] Jul. 31, 2019.
Spetlik et al., "Visual Heart Rate Estimation with Convolutional Neural Network," British Machine Vision Conference, 12 pages (2018).

\* cited by examiner

SYSTEM AND METHOD FOR TRAINING A REMOTE PHOTOPLETHYSMOGRAPHY MODEL

CROSS-REFERENCE TO RELATED APPLICATION

This application claims the benefit of U.S. Provisional Patent Application No. 63/161,799, entitled "SYSTEM AND METHOD FOR LEARNING TO ESTIMATE HEART RATE FROM UNLABELED VIDEO," filed Mar. 16, 2021, which is incorporated by reference herein in its entirety.

TECHNICAL FIELD

The subject matter described herein relates, in general, to systems and methods for training video information models, such as remote photoplethysmography ("PPG") models.

BACKGROUND

The background description provided is to present the context of the disclosure generally. Work of the inventor, to the extent it may be described in this background section, and aspects of the description that may not otherwise qualify as prior art at the time of filing, are neither expressly nor impliedly admitted as prior art against the present technology.

Several different methodologies exist for measuring the physiological state of a person. For example, electrocardiograms require the placement of electrodes on the skin of a person. These electrodes detect small electrical changes resulting from cardiac muscle depolarization followed by repolarization during each heartbeat.

Traditional PPG is an optical technique used to detect volumetric changes in blood in peripheral circulation. These traditional PPG systems may use low-intensity infrared light that travels through biological tissues and is absorbed by bones, skin pigments, and venous and arterial blood. Since light is more strongly absorbed by blood than the surrounding tissues, the changes in blood flow can be detected by changes in the intensity of light by PPG sensors placed on the subject's skin.

More recently, systems that perform remote PPG have been developed. Unlike electrocardiograms and traditional PPG systems, these systems do not require the placement of a light source and/or sensors on the subject's skin. Remote PPG systems can remotely measure changes in transmitted or reflected light from the body due to volumetric changes in blood flow using a standard imaging device, such as a camera. To correctly process imaging information, Remote PPG systems require the use of either highly specialized discrete algorithms or utilize models that have been trained with supervised deep learning approaches.

SUMMARY

This section generally summarizes the disclosure and is not a comprehensive explanation of its full scope or all its features.

In one embodiment, a system for training a remote PPG model that outputs a subject PPG signal based on a subject video clip of a subject includes a processor and a memory in communication with the processor. The memory may include a training module having instructions that, when executed by the processor, cause the processor to train the remote PPG model in a self-supervised contrastive learning manner using an unlabeled video clip having a sequence of images of a face of a person.

In another embodiment, a method for training a remote PPG model that outputs a subject PPG signal based on a subject video clip of a subject includes the step of training the remote PPG model in a self-supervised contrastive learning manner using an unlabeled video clip having a sequence of images of a face of a person.

In yet another embodiment, a non-transitory computer-readable medium includes instructions that, when executed by a processor, cause the processor to train a remote PPG model in a self-supervised contrastive learning manner using an unlabeled video clip having a sequence of images of a face of a person. Like before, the remote PPG model is configured to output a subject PPG signal based on a subject video clip of a subject.

Further areas of applicability and various methods of enhancing the disclosed technology will become apparent from the description provided. The description and specific examples in this summary are intended for illustration only and are not intended to limit the scope of the present disclosure.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements, or multiple elements may be designed as one element. In some embodiments, an element shown as an internal component of another element may be implemented as an external component and vice versa. Furthermore, elements may not be drawn to scale.

DETAILED DESCRIPTION

Described is a system and method for training a model utilized by a remote PPG system. The system and method train the model in a self-supervised contrastive learning manner. This has advantages over other systems in that unlabeled video clips can be utilized to train the model. Current systems utilize self-supervised deep learning techniques that required labeled video clips, which can be unavailable or difficult to develop.

Figure 1:
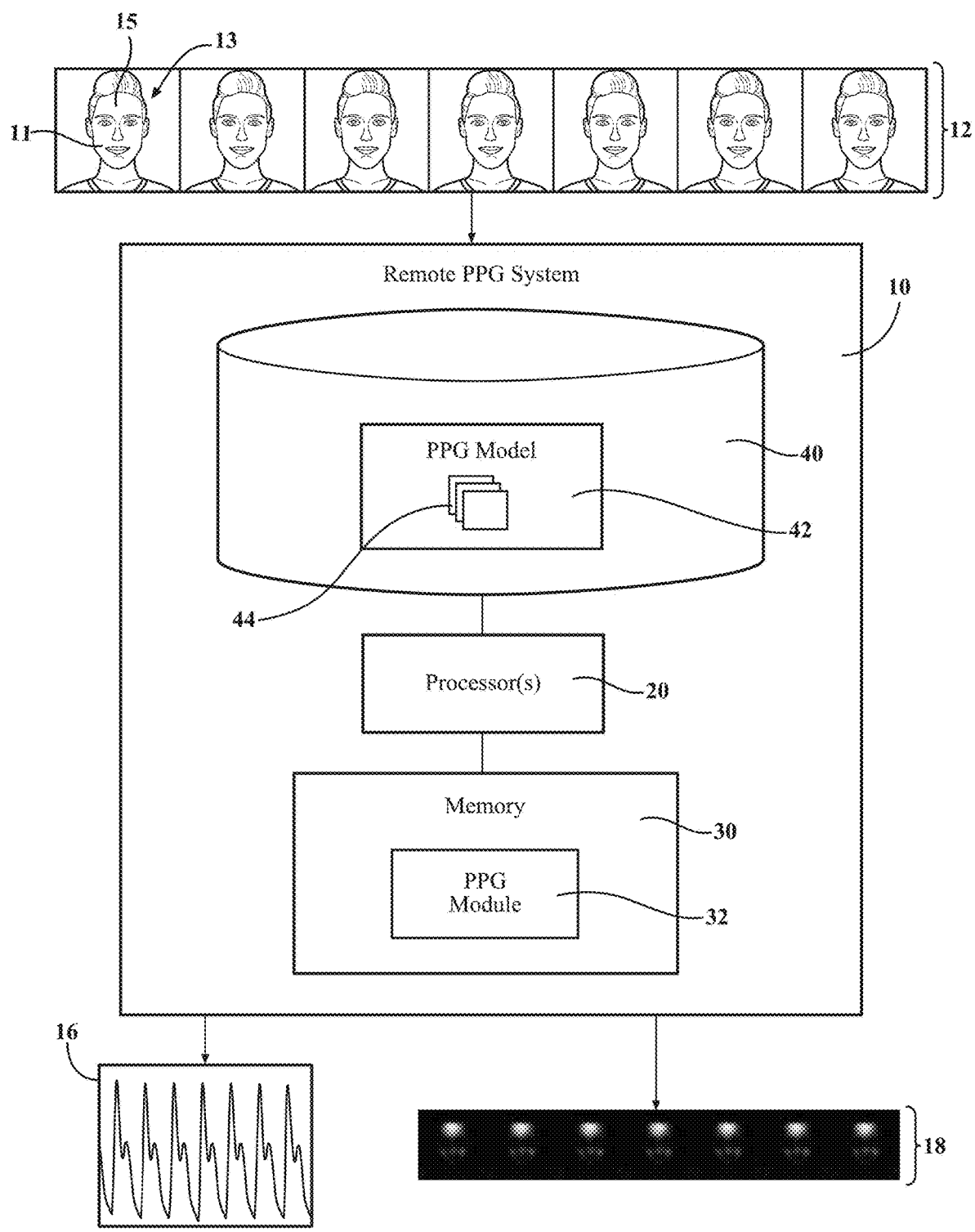
FIG. 1 illustrates a remote PPG system that can determine a heart rate of a subject from a video clip and, optionally, determine a saliency signal indicating where in the video clip a PPG signal from the subject is strongest.

To better understand how the system and method train a model for a remote PPG system, a brief description of one example of a remote PPG system will be provided. Referring to FIG. 1, illustrated is a remote PPG system 10 that receives a video clip 12 that includes images of a face 11 of a subject 13. The video clip 12 may be a sequential video clip captured by an imaging device, such as a camera. The camera utilized to capture the video clip 12 may be any type of camera capable of capturing images, such as traditional cameras, high-definition cameras, infrared cameras, and the like. The video clip 12 may be a stored video clip that is provided to the remote PPG system 10 or may be a real-time video clip that is captured in real-time and provided to the remote PPG system 10.

Upon receiving the video clip 12, the remote PPG system 10 can utilize information extracted from the video clip 12 and output a heart rate signal 16. Optionally, the remote PPG system 10 may also output a saliency signal 18, indicating where the PPG signal is strongest in the video clip 12. For example, the saliency signal 18 indicates that the remote PPG signal is strongest on a forehead 15 of the subject 11. Information from the saliency signal can be utilized to determine how well the remote PPG system 10 is working and/or if there any issues with the video clip 12 provided to the remote PPG system 10. For example, if the saliency signal 18 indicates a very weak PPG signal, the subject 11 may be repositioned with respect to the camera to improve the strength of the saliency signal 18, which results in a more accurate heart rate signal 16 predicted by the remote PPG system 10.

The remote PPG system 10 can take anyone of a number of different forms. In this example, the remote PPG system 10 includes one or more processor(s) 20. The processor(s) 20 can be a single processor or may be multiple processors working in concert. Furthermore, the processor(s) 20 may be located within the remote PPG system 10 or may be located remotely from the remote PPG system 10. For example, the processor(s) 20 may be partially or entirely located in a separate external device or remote device, such as a cloud computing device.

The processor(s) 20 may be in communication with a memory 30 that includes a PPG module 32. The PPG module 32 includes instructions that cause the processor(s) 20 to interpret the video clip 12 to output the heart rate signal 16 and/or the saliency signal 18. In addition, the remote PPG system 10 may also include a data store 40 that may be combined with the memory 30, or separate and apart from the memory 30 is shown. Here, the data store 40 includes a PPG model 42 that includes one or more model weights 44.

The PPG model 42 may be any one of a number of different neural networks that can interpret the video clip 12 and process the video clip 12 to output the heart rate signal 16 and/or the saliency signal 18. The model weights 44 may be one or more model weights that, based on their adjustments, impact how the PPG model 42 interprets the video clip 12 and outputs the heart rate signal 16 and/or the saliency signal 18. Generally, the model weights 44 are the parameters of the PPG model 42, which are used in the layers of the PPG model 42. As such, adjustment of the model weights 44 can result in the optimization of the PPG model 42 such that the PPG model 42 outputs a more accurate heart rate signal 16 and/or saliency signal 18.

The PPG model 42 may take any one of a number of different forms and may use any one of a number of different models with different layers arranged in a number of different ways. In one example, the encoder and decoder of the PPG model 42 are detailed in the following chart.

|  | in | out | kernel | stride | pad |
|---|---|---|---|---|---|
| ENCODER |  |  |  |  |  |
| Conv3d + BN3d + ELU | C | 32 | (1, 5, 5) | 1 | (0, 2, 2) |
| AvgPool3d |  |  | (1, 2, 2) | (1, 2, 2) | 0 |
| Conv3d + BN3d + ELU | 32 | 64 | (3, 3, 3) | 1 | (1, 1, 1) |
| Conv3d + BN3d + ELU | 64 | 64 | (3, 3, 3) | 1 | (1, 1, 1) |
| AvgPool3d |  |  | (2, 2, 2) | (2, 2, 2) | 0 |
| Conv3d + BN3d + ELU | 64 | 64 | (3, 3, 3) | 1 | (1, 1, 1) |
| Conv3d + BN3d + ELU | 64 | 64 | (3, 3, 3) | 1 | (1, 1, 1) |
| AvgPool3d |  |  | (2, 2, 2) | (2, 2, 2) | 0 |
| Conv3d + BN3d + ELU | 64 | 64 | (3, 3, 3) | 1 | (1, 1, 1) |
| Conv3d + BN3d + ELU | 64 | 64 | (3, 3, 3) | 1 | (1, 1, 1) |
| AvgPool3d |  |  | (1, 2, 2) | (1, 2, 2) | 0 |
| Conv3d + BN3d + ELU | 64 | 64 | (3, 3, 3) | 1 | (1, 1, 1) |
| Conv3d + BN3d + ELU | 64 | 64 | (3, 3, 3) | 1 | (1, 1, 1) |
| DECODER |  |  |  |  |  |
| Interpolate |  |  | (2, 1, 1) |  |  |
| Conv3d + BN3d + ELU | 64 | 64 | (3, 1, 1) | 1 | (1, 0, 0) |
| Interpolate |  |  | (2, 1, 1) |  |  |
| Conv3d + BN3d + ELU | 64 | 64 | (3, 1, 1) | 1 | (1, 0, 0) |
| AdaptiveAvgPool3d |  |  | (—, 1, 1) |  |  |
| Conv3d | 64 | 1 | (1, 1, 1) | 1 | (0, 0, 0) |

The core of the PPG model 42 above includes a series of eight 3D convolutions with a kernel of (3, 3, 3), 64 channels, and ELU activation. This allows for the PPG model 42 to learn spatio-temporal features over the input video clip. Average pooling and batch normalization are also employed between the layers. The PPG model 42 also employs upsampling interpolation (x4) and a 3D convolution with a (3, 1, 1) kernel. This upsampling step is repeated twice and removes the aliasing in the output. Next, the PPG model 42 performs adaptive average pooling to collapse the spatial dimension and produce a 1D signal. A final 1D convolution is applied to convert the 64 channels to the output single-channel PPG.

The PPG model 42 that determines the saliency signal 18 may follow a Resnet-18 structure, truncated after layer 1, with pre-trained ImageNetweights. Each BasicBlock consists of a 3×3 convolution, 2D batch normalization, ReLU, 3×3 convolution, 2D batch normalization, addition with the BasicBlock input (the residual), and a final ReLU. The chart below illustrates the architecture of this network.

| SALIENCY NET | in | out | kernel | stride | pad |
|---|---|---|---|---|---|
| Conv2d + BN2d + ReLU | C | 64 | (1, 7, 7) | 2 | 3 |
| MaxPool |  |  | (1, 3, 3) | 2 | 1 |
| BasicBlock | 64 | 64 |  | 1 |  |
| BasicBlock | 64 | 64 |  | 1 |  |
| BasicBlock | 64 | 64 |  | 1 |  |

Again, it should be understood that the PPG model 42 may take any one of a number of different forms and not necessarily those specifically illustrated and described above.

Figure 2:
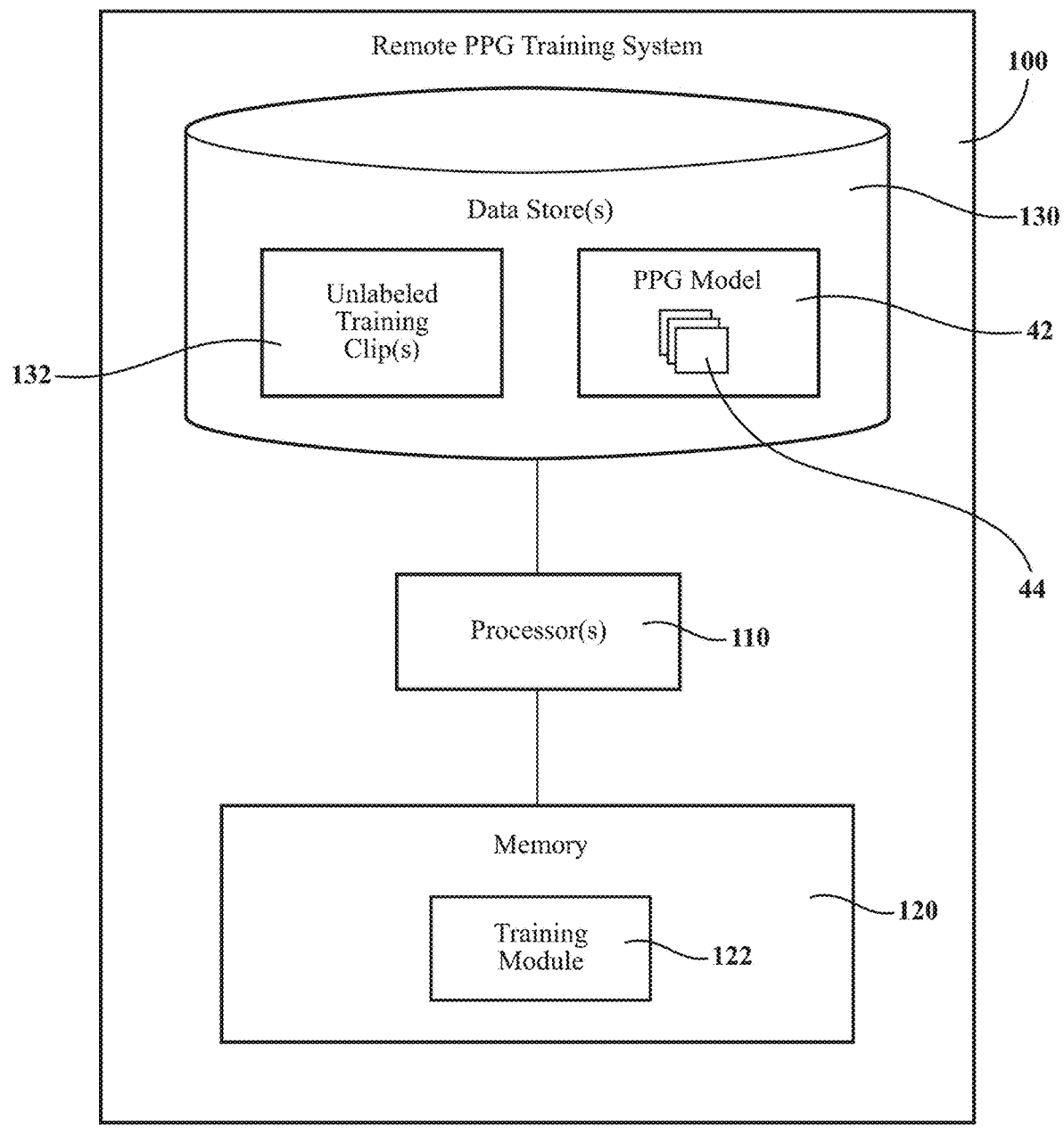
FIG. 2 illustrates a remote PPG training system for training the model utilized by the remote PPG system.

As stated before, the PPG model 42 is trained in a self-supervised contrastive learning manner using unlabeled video clips. FIG. 2 illustrates one example of a remote PPG training system 100 for training the PPG model 42. The remote PPG training system 100 may be incorporated within the remote PPG system 10 of FIG. 1 or may be separate as shown.

As shown, the remote PPG training system 100 includes one or more processor(s) 110. Accordingly, the processor(s) 110 may be a part of the remote PPG training system 100, or the remote PPG training system 100 may access the processor(s) 110 through a data bus or another communication path. In one or more embodiments, the processor(s) 110 is an application-specific integrated circuit that is configured to implement functions associated with a training module 122. In general, the processor(s) 110 is an electronic processor such as a microprocessor that is capable of performing various functions as described herein. In one embodiment, the remote PPG training system 100 includes a memory 120 that stores the training module 122. The memory 120 is a random-access memory ("RAM"), read-only memory ("ROM"), a hard disk drive, a flash memory, or other suitable memory for storing the training module 122. The training module 122 is, for example, computer-readable instructions that, when executed by the processor(s) 110, cause the processor(s) 110 to perform the various functions disclosed herein, namely training the PPG model 42.

Furthermore, in one embodiment, the remote PPG training system 100 includes a data store(s) 130. The data store(s) 130 is, in one embodiment, an electronic data structure such as a database that is stored in the memory 120 or another memory and that is configured with routines that can be executed by the processor(s) 110 for analyzing stored data, providing stored data, organizing stored data, and so on. Thus, in one embodiment, the data store(s) 130 stores data used by the training module 122 in executing various functions. In one embodiment, the data store(s) 130 includes the PPG model 42 to be trained.

As explained previously, the PPG model 42 may include one or more model weights 44 that are adjusted as the PPG model 42 is trained by the remote PPG training system 100. The data store(s) 130 may also include an unlabeled video clip 132 used to train the PPG model 42. The unlabeled video clip 132 may be a single video clip or may be multiple video clips. As will be explained later in this description, the PPG model 42 can be trained in a self-supervised contrastive learning manner utilizing unlabeled data in the form of unlabeled video clip 132. The unlabeled video clip 132 may be similar to the video clip 12 shown in FIG. 1, wherein unlabeled video clip 132 include the face of the subject.

Figure 3:
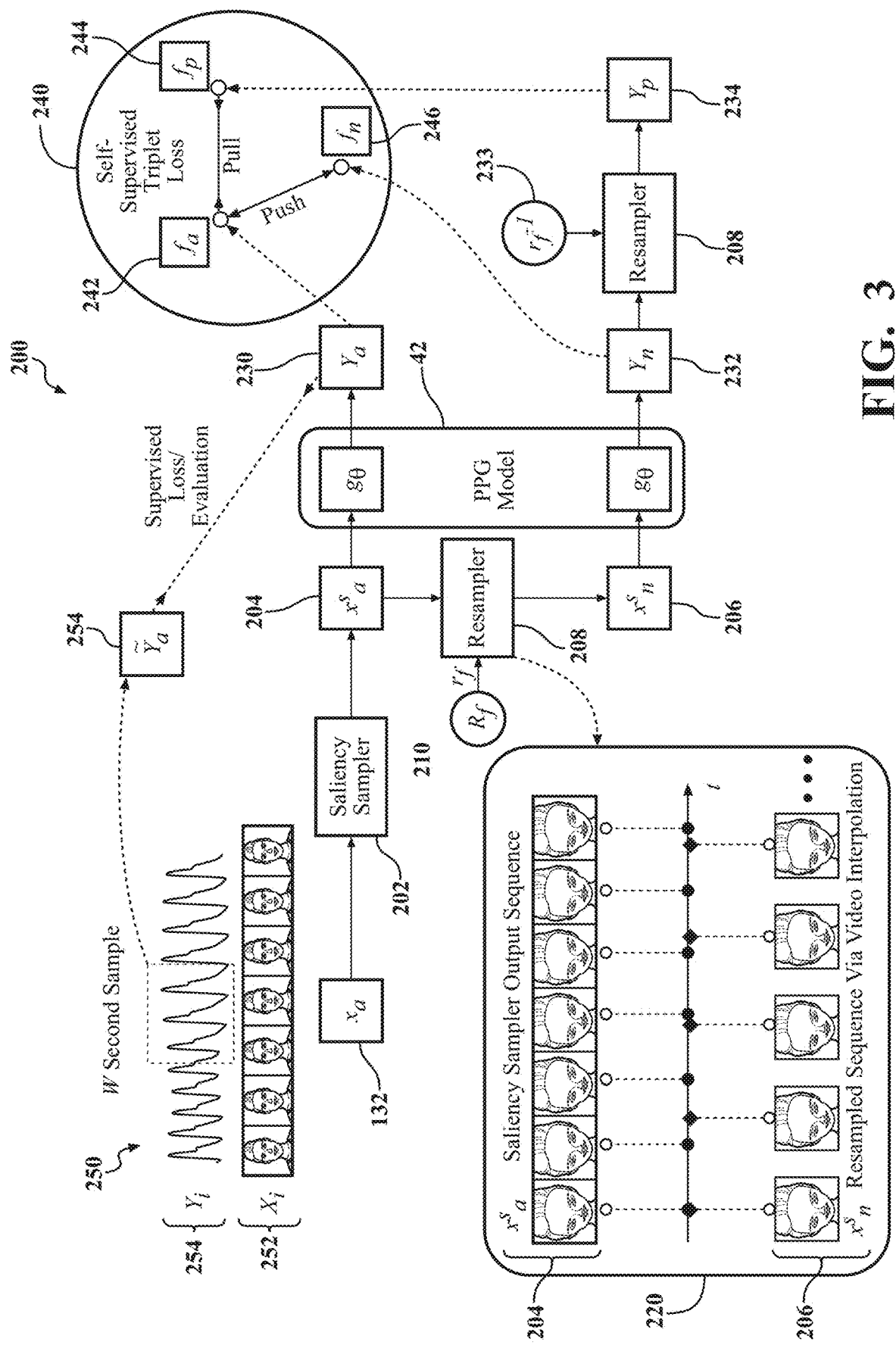
FIG. 3 illustrates a process flow indicating how the remote PPG training system trains the model.

Regarding the training module 122, the training module 122 includes instructions that cause the processor(s) 110 to train the PPG model 42 using the unlabeled video clip 132. To better illustrate how this occurs, reference is made to FIG. 3, which illustrates a process flow 200 indicating how the PPG model 42 is trained using the unlabeled video clips 132 ($x_a$) by the PPG training system 100. Generally, as a preprocessing step, the processor(s) 110 may estimate a bounding box around the face of the subject in the unlabeled video clips 132 ($x_a$). The processor(s) 110 may add an additional 50% scale buffer to the bounding box before extracting a frame, which may be 192×128 frame. Of course, it should be understood that the scaling and size of the frame may vary from application to application. The bounding box location may be updated in the subsequent frames of the unlabeled video clips 132 if a new non-buffered bounding box outside a larger one. The bounding box may be cropped and scaled to a 64×64 resolution.

In one example, the training module 122 includes instructions that cause the processor(s) 110 to warp the unlabeled video clip 132 ($x_a$) by passing the unlabeled video clip 132 ($x_a$) through a saliency sampler 202 to generate a warped unlabeled video clip 204 ($x^s_a$). It should be understood that the passing of the unlabeled video clip 132 ($x_a$) through the saliency sampler 202 may be an optional step that does not necessarily need to occur. The use of the saliency sampler 202 may be advantageous to provide transparency as to what the PPG model 42 is learning and to warp the input image to spatially emphasize task-salient regions before passing it onto PPG model 42.

In one example, the saliency sampler 202 may use a pre-trained ResNet-18, truncated after the conv2× block. Optionally, the following two additional loss terms may be:

$$\mathcal{L}_{sparsity} = -\frac{1}{ND} \sum_i^D \sum_j^N s_i^j \log(s_i^j) \quad (1)$$

$$\mathcal{L}_{sparsity} = -\frac{1}{ND} \sum_i^D \sum_j^N s_i^j \log(s_i^j) \quad (2)$$

$$\mathcal{L}_{saliency} = w_s \mathcal{L}_{sparsity} + w_t \mathcal{L}_{temporal} \quad (3)$$

where $s_i^j$ is the value of the per-frame softmax-normalized saliency map at frame i in the sequence and position j in the frame, $d^j_{i,i+1}$ is the difference between saliency pixel j from frame i to i+1, N is the number of pixels in a frame, and D is the number of frames in the video sequence. The sparsity term favors solutions that have lower entropy (i.e., are spatially sparse, such as the forehead 15 of the subject 11 of FIG. 1), while the temporal consistency favors solutions that are smooth from frame to frame.

Again, as stated before, the use of the saliency sampler 202 is optional and does not need to be utilized. As such, the warped unlabeled video clip 204 ($x^s_a$) of FIG. 3 may simply be the unlabeled video clip 132 ($x^s_a$) if the saliency sampler 202 is not utilized. The training module 122 may then cause the processor(s) 110 to then pass the warped unlabeled video clip 204 ($x^s_a$) (which may be simply the unlabeled video clip 132 ($x_a$) if the saliency sampler 202 is not utilized) through the PPG model 42 to generate an anchor PPG signal 230 ($y_a$).

The training module 122 may cause the processor(s) 110 to resample the warped unlabeled video clip 204 ($x^s_a$) using a trilinear resampler 208 at a first frequency ratio 210 ($R_f$) to generate a negative sample clip 206 ($x^s_n$). Again, instead of resampling the warped unlabeled video clip 204 ($x^s_a$), the unlabeled video clip 132 ($x_a$) may be resampled instead if the saliency sampler 202 is not utilized. The first frequency ratio 210 ($R_f$) may be between 66% to 80%. The training module 122 may also cause the processor(s) 110 to pass the negative sample clip 206 ($x^s_n$) through the PPG model 42 to generate a negative PPG signal 232 ($y_n$).

Once generating the negative PPG signal 232 ($y_n$), the training module 122 may cause the processor(s) 110 to resample the negative PPG signal 232 ($y_n$) using the trilinear resampler 208 at a second frequency ratio 233 ($R_f^{-1}$) to generate a positive PPG signal 234 ($y_p$). The second frequency ratio may be the inverse of the first frequency ratio. The training module 122 may cause the processor(s) 110 to adjust the model weights 44 of the PPG model 42 based on a first loss calculated. The first calculated loss is determined using a first loss function that considers the anchor PPG signal 230 ($y_a$), the negative PPG signal 232 ($y_n$), and the positive PPG signal 234 ($y_p$).

As explained previously, the PPG model 42 is trained in a self-supervised contrastive learning manner using a self-supervised triplet loss function 240. In this example, the training module 122 causes the processor(s) 110 to generate anchor subset views 242 ($f_a$) based on the anchor PPG signal 230 ($y_a$), negative subset views ($f_n$) 246 based on the negative PPG signal 232 ($y_n$), and positive subset views 244 ($f_p$) based on the positive PPG signal 234 ($y_p$). The anchor subset views 242 ($f_a$), negative subset views 246 ($f_n$), and positive subset views 244 ($f_p$) may have one or more views that correspond to each other. Moreover, from the anchor PPG signal 230 ($y_a$), the negative PPG signal 232 ($y_n$), and the positive PPG signal 234 ($y_p$), the training module 122 cause the processor(s) 110 to take $V_N$ subset views of length $V_L$. This enforces an assumption that a heart rate is relatively stable within a certain window. Because of this, the signal within each view should appear similar.

The training module 122 may cause the processor(s) 110 to calculate the distance between all combinations. In this example, the training module 122 causes the processor(s) 110 to determine a positive total ($P_{tot}$) based on a distance between corresponding anchor subset views 242 ($f_a$) and positive subset views 244 ($f_p$) and determine a negative total ($N_{tot}$) based on a distance between corresponding anchor subset views 242 ($f_a$) and negative subset views ($f_n$) 246. Next, the training module 122 causes the processor(s) 110 to determine the difference between the positive total ($P_{tot}$) and the negative total ($N_{tot}$) to generate a loss. Optionally, the loss may be scaled by the total number of views ($V^2N$).

The training module 122 may use the power spectral density mean squared error as the distance metric between the positive total ($P_{tot}$) and the negative total ($N_{tot}$) signals when performing contrastive training with multi-view triplet loss. The training module 122 may cause the processor(s) 110 to calculate the power spectral density for each signal and zero out all frequencies outside the relevant heart rate range from 40 to 250 beats per minute ("bpm"). The training module 122 may cause the processor(s) 110 to normalize each to have a sum of one and compute the mean squared error between them. Finally, the training module 122 may cause the processor(s) 110 the irrelevant power ratio as a validation metric during contrastive training. The training module 122 may cause the processor(s) 110 to first calculate the power spectral density and split it into the relevant (40 to 250 bpm) and irrelevant frequencies. The training module 122 may cause the processor(s) 110 to divide the power in the irrelevant range with the total power. Irrelevant power ratio can be used as an unsupervised measure of signal quality.

Using the loss, the training module 122 may cause the processor(s) 110 to adjust the model weights 44 of the PPG model 42. As such, the process flow 200 illustrates a methodology for training the PPG model 42 using unlabeled video clips 132 in a self-supervised contrasting learning manner. The use of unlabeled training clips is advantageous in that it does not require expensive and hard to acquire annotated data for training the PPG model 42. As such, the PPG model 42 can be trained solely with unlabeled training clips.

However, in addition to training the PPG model 42 with unlabeled training clips, it is also possible to fine-tune the PPG model 42 by additionally training the PPG model 42 and in a supervised manner. For example, the process flow 200 also illustrates annotated data 250 in the form of a video clip 252 that has been annotated with a ground truth PPG signal 254 ($\tilde{y}_a$). The video clips 252 may replace the unlabeled video clips 132 and be provided to the PPG model 42 to output the anchor PPG signal 230 ($y_a$). Differences between the ground truth PPG signal 254 ($\tilde{y}_a$) and the anchor PPG signal 230 ($y_a$) may then be utilized to adjust one or more model weights 44 of the PPG model 42 to minimize the loss of one or more particular loss functions. Different types of supervised loss functions may be utilized to fine-tune the PPG model 42. For example, the supervised loss functions could include Pearson's correlation loss function, a signal-to-noise ratio loss function, and/or a maximum cross-correlation loss function.

A Pearson's correlation loss function may be used as a baseline supervised loss and validation metric. While it is scale invariant, it assumes perfect temporal synchronization between the ground truth and observed data. Otherwise, the PPG model 42 must be capable of learning a temporal offset, assuming the offset is constant.

A signal-to-noise ratio loss function may be used as another baseline that trains the remote PPG model 42 to match the ground truth PPG signal 254 ($\tilde{y}_a$) instead of the full PPG signal. It relaxes the alignment assumption by expressing the loss in the frequency domain using the power spectral density. It calculates the amount of power in the target heart rate frequency bin of the power spectral density and compares it to the total other power in the PPG signal. Because of this, it assumes that all other frequencies should be zeroed out, which may remove meaningful harmonics.

A maximum cross-correlation ("MCC") loss may be computed in the frequency domain as follows:

$$MCC = c_{pr} \times \text{Max}\left(\frac{F^{-1}\{BPass(F\{y\} \cdot F\{\hat{y}\})\}}{\sigma_y \times \sigma_{\hat{y}}}\right) \quad (4)$$

Moreover, the training module 122 may cause the processor(s) 110 to subtract a means of the anchor PPG signal 230 ($y_a$) and the ground truth PPG signal 254 ($\tilde{y}_a$) from the anchor PPG signal 230 ($y_a$) and the ground truth PPG signal 254 ($\tilde{y}_a$). The training module 122 may cause the processor(s) 110 to determine a cross-correlation of the anchor PPG signal 230 ($y_a$) and the ground truth PPG signal by taking a fast Fourier transform ("FFT") of the anchor PPG signal 230 ($y_a$) and the ground truth PPG signal 254 ($\tilde{y}_a$) and multiplying one of the anchor PPG signal and the ground truth PPG signal with a conjugate of the other. This is equivalent to convolution in the time domain. The training module 122 may cause the processor(s) 110 to zero-pad the inputs to the FFT to twice their length to prevent circular correlation.

The training module 122 may cause the processor(s) 110 to filter the cross-correlation to remove cross-correlations outside a range of an expected heart rate (40 to 250 bpm) to generate a filtered spectrum of cross-correlation. The training module 122 may cause the processor(s) 110 to determine a final cross-correlation by taking an inverse of the FFT of the filtered spectrum of cross-correlation and dividing by standard deviations of the anchor PPG signal 230 ($y_a$) and the ground truth PPG signal 254 ($\tilde{y}_a$). A maximum of the final cross-correlation is the loss. The MCC may be scaled by a constant ($c_{pr}$) which is the inverse ratio of the power inside the relevant heart rate frequencies. This ensures that the MCC is unaffected by the frequencies outside the relevant range. The training module 122 may cause the processor(s) 110 to use the loss to adjust one or more model weights 44 of the PPG model 42.

Figure 4:
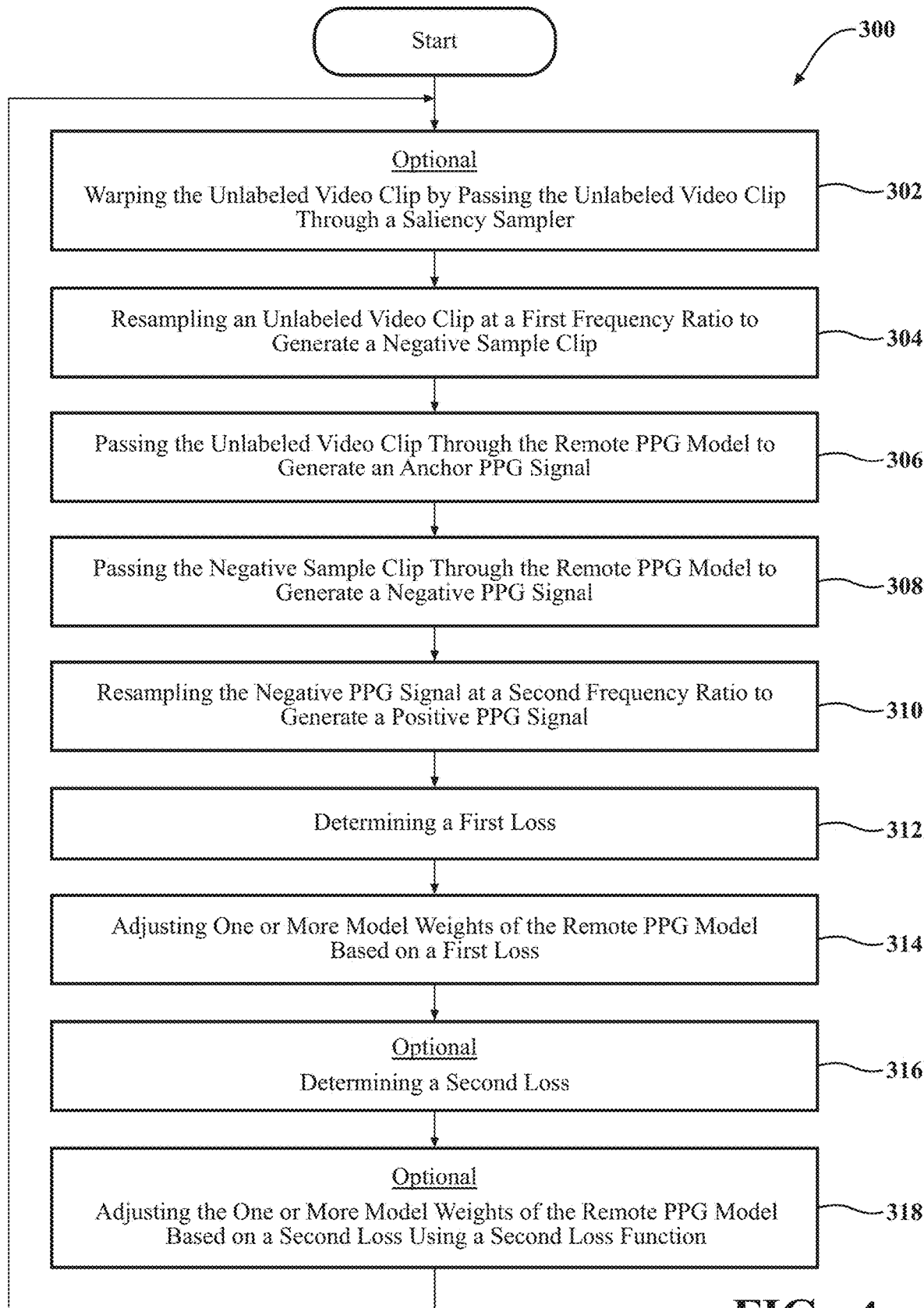
FIG. 4 illustrates a method for training the model utilized by the remote PPG system.

Referring to FIG. 4, a method 300 for training a remote PPG system is shown. The method 300 will be described from the viewpoint of the remote PPG training system 100 of FIG. 2 and the process flow 200 of FIG. 2. However, it should be understood that this is just one example of implementing the method 300. While method 300 is discussed in combination with the remote PPG training system 100, it should be appreciated that the method 300 is not limited to being implemented within the remote PPG training system 100 but is instead one example of a system that may implement the method 300.

In step 302, the training module 122 includes instructions that cause the processor(s) 110 to warp the unlabeled video clip 132 ($x_a$) by passing the unlabeled video clip 132 ($x_a$) through a saliency sampler 202 to generate a warped unlabeled video clip 204 ($x^s_a$). As explained previously, this step may be optional.

In step 304, the training module 122 may cause the processor(s) 110 to resample the warped unlabeled video clip 204 ($x^s_a$) or unlabeled video clip 132 ($x_a$) using a trilinear resampler 208 at a first frequency ratio 210 ($R_f$) to generate a negative sample clip 206 ($x^s_n$).

In step 306, the training module 122 may cause the processor(s) 110 to pass the warped unlabeled video clip 204 ($x^s_a$) or unlabeled video clip 132 ($x_a$) through the PPG model 42 to generate an anchor PPG signal 230 ($y_a$). Similarly, in step 308, the training module 122 may also cause the processor(s) 110 to pass the negative sample clip 206 ($x^s_n$) the PPG model 42 to generate a negative PPG signal 232 ($y_n$).

In step 310, the training module 122 may cause the processor(s) 110 to resample the negative PPG signal 232 ($y_n$) using the trilinear resampler 208 at a second frequency ratio 233 ($R_f^{-1}$) to generate a positive PPG signal 234 ($y_p$). As explained, previously, the second frequency ratio may be the inverse of the first frequency ratio.

In step, 312 the training module 122 may cause the processor(s) 110 to determine a first loss using a first loss function. The first loss is then used to adjust the model weights 44 of the PPG model 42, as shown in step 314. The steps for determining the first loss are shown in FIG. 5, which will be described later.

Figure 6:
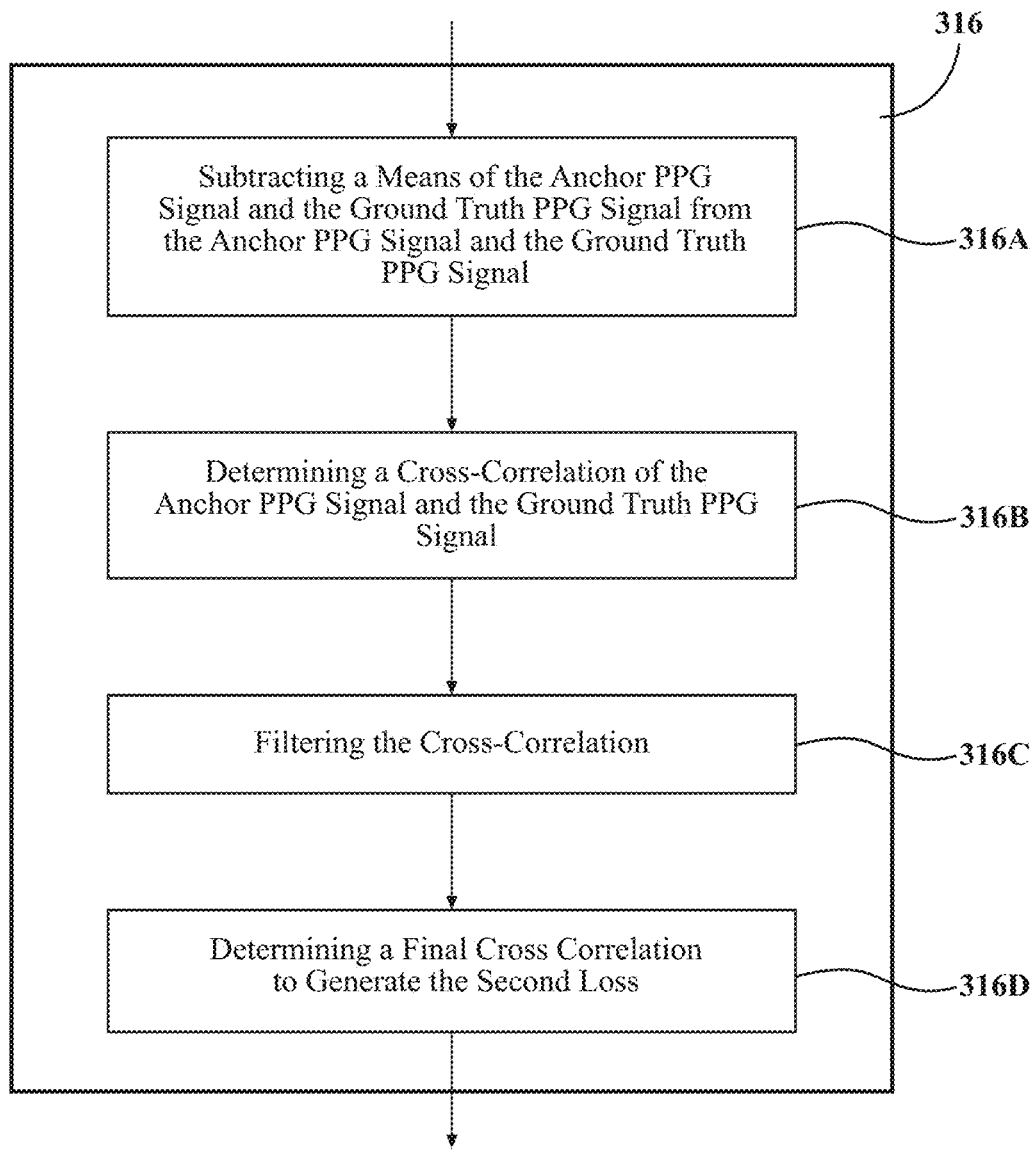
FIG. 6 illustrates an optional method for fine-tuning the model utilized by the remote PPG system using supervised learning.

In step 316, which may be optional, the training module 122 may cause the processor(s) 110 to determine a second loss using a second loss function. Generally, the second loss is used to fine-tune the PPG model 42 and may utilize labeled clips. The steps for determining the second loss are shown in FIG. 6, which will be described later. In step 318, which also may be optional, the training module 122 may cause the processor(s) 110 to adjust the model weights 44 of the PPG model 42 based on the second loss. Thereafter, the method 300 may end or return to step 302.

Figure 5:
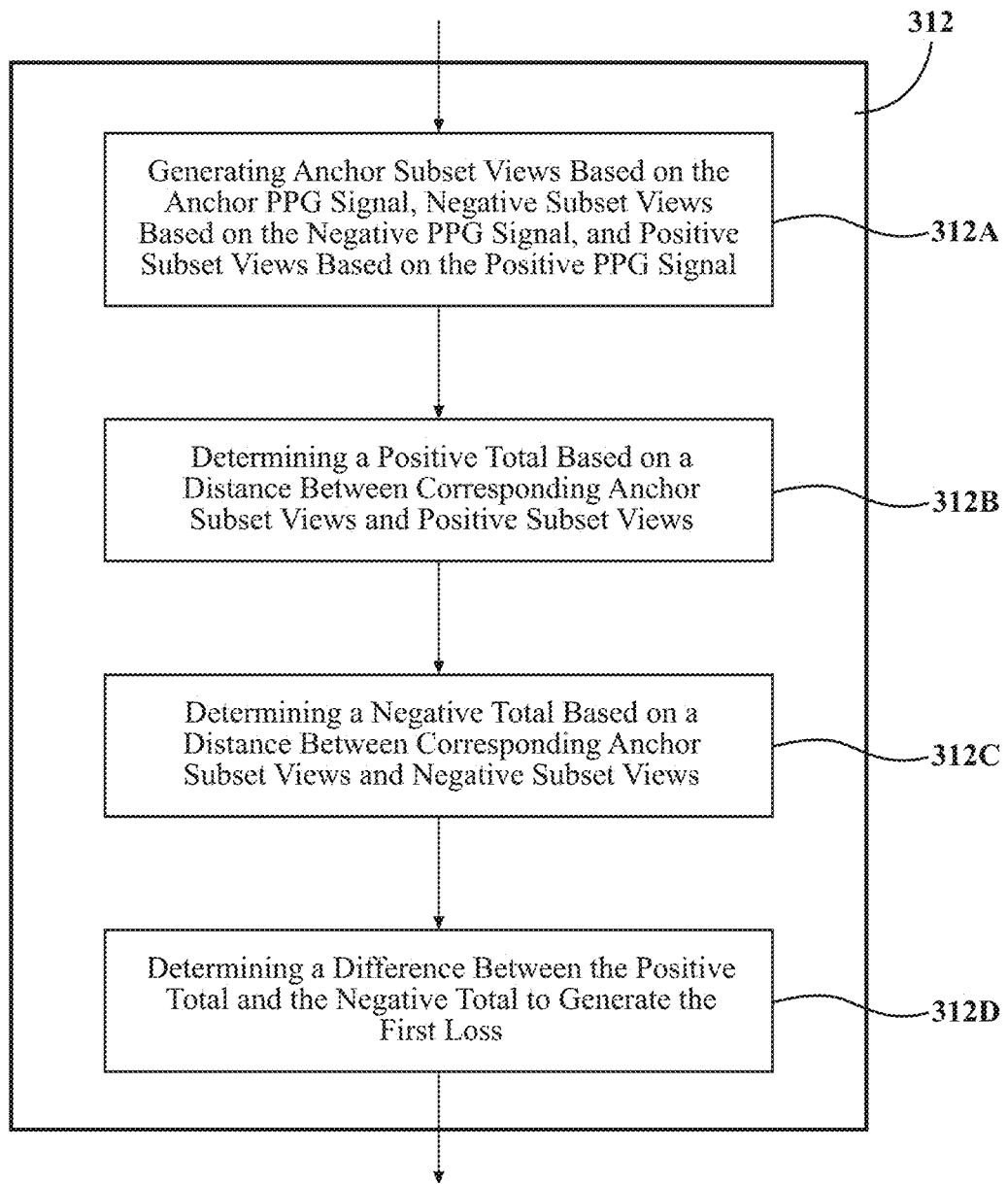
FIG. 5 illustrates a method for determining a loss using self-supervised contrastive learning to train the model utilized by the remote PPG system.

Regarding determining the first loss of step 312, reference is made to FIG. 5, which illustrates the steps to determine the first loss. In step 312A, the training module 122 may cause the processor(s) 110 to generate anchor subset views 242 ($f_a$) based on the anchor PPG signal 230 ($y_a$), negative subset views ($f_n$) 246 based on the negative PPG signal 232 ($y_n$), and positive subset views 244 ($f_p$) based on the positive PPG signal 234 ($y_p$). As explained previously, the anchor subset views 242 ($f_a$), negative subset views ($f_n$) 246, and positive subset views 244 ($f_p$) may have one or more views that correspond to each other.

In step 312B, the training module 122 may cause the processor(s) 110 to determine a positive total ($P_{tot}$) based on a distance between corresponding anchor subset views 242 ($f_a$) and positive subset views 244 ($f_p$). Similarly, in step 312C, the training module 122 may cause the processor(s) 110 to determine a negative total ($N_{tot}$) based on a distance between corresponding anchor subset views 242 ($f_a$) and negative subset views ($f_n$) 246.

In step 312D, the training module 122 may cause the processor(s) 110 to determine the difference between the positive total ($P_{tot}$) and the negative total ($N_{tot}$) to generate the first loss. The first loss may be scaled by the total number of views ($V^2_N$).

Regarding determining the second loss of step 316, reference is made to FIG. 6, which illustrates the steps to determine the second loss. In step 316A, the training module 122 may cause the processor(s) 110 to subtract a means of the anchor PPG signal 230 ($y_a$) and the ground truth PPG signal 254 ($\tilde{y}_a$) from the anchor PPG signal 230 ($y_a$) and the ground truth PPG signal 254 ($\tilde{y}_a$). T In step 316B, the training module 122 may cause the processor(s) 110 to determine a cross-correlation of the anchor PPG signal 230 ($y_a$) and the ground truth PPG signal by taking an FFT of the anchor PPG signal 230 ($y_a$) and the ground truth PPG signal 254 ($\tilde{y}_a$) and multiplying one of the anchor PPG signal and the ground truth PPG signal with a conjugate of the other. This is equivalent to convolution in the time domain. The training module 122 may cause the processor(s) 110 to zero-pad the inputs to the FFT to twice their length to prevent circular correlation.

In step 316C, the training module 122 may cause the processor(s) 110 to filter the cross-correlation to remove cross-correlations outside a range of an expected heart rate (40 to 250 bpm) to generate a filtered spectrum of cross-correlation. In step 316D, the training module 122 may cause the processor(s) 110 to determine a final cross-correlation by taking an inverse of the FFT of the filtered spectrum of cross-correlation and dividing by standard deviations of the anchor PPG signal 230 ($y_a$) and the ground truth PPG signal 254 ($\tilde{y}_a$). A maximum of the final cross-correlation is the second loss.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-6, but the embodiments are not limited to the illustrated structure or application.

According to various embodiments, the flowcharts and block diagrams in the figures illustrate the architecture, functionality, and operation of possible implementations of systems, methods, and computer program products. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components, and/or processes also can be embedded in a computer-readable storage, such as a computer program product or other data programs storage device, readable by a machine, tangibly embodying a program of instructions executable by the machine to perform methods and processes described herein. These elements can also be embedded in an application product that comprises all the features enabling the implementation of the methods described herein and, when loaded in a processing system, can carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive ("HDD"), a solid-state drive ("SSD"), a ROM, an erasable programmable read-only memory (EPROM or Flash memory), a portable compact disc read-only memory ("CD-ROM"), a digital versatile disc ("DVD"), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, module as used herein includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit ("ASIC"), a hardware component of a system on a chip ("SoC"), as a programmable logic array ("PLA"), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

As used herein, the terms "a" and "an" are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC, or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A system for training a remote photoplethysmography ("PPG") model that outputs a subject PPG signal based on a subject video clip of a subject, the system comprising: a processor; and a memory in communication with the processor, the memory having a training module having instructions that, when executed by the processor, cause the processor to train the remote PPG model in a self-supervised contrastive learning manner using an unlabeled video clip having a sequence of images of a f ace of a person;
wherein the training module further includes instructions that, when executed by the processor, cause the processor to:
resample the unlabeled video clip at a first frequency ratio to generate a negative sample clip;
pass the unlabeled video clip through the remote PPG model to generate an anchor PPG signal;
pass the negative sample CIO through the remote PPG model to generate a negative PPG signal;
resample the negative PPG signal at a second frequency ratio to generate a positive PPG signal, wherein the second frequency ratio is an inverse of the first frequency ratio; and
adjust one or more model weights of the remote PPG model based on a first loss calculated using a first loss function that considers the anchor PPG signal, the negative PPG signal, and the positive PPG signal.

2. The system of claim 1, wherein the remote PPG model is configured to output a saliency signal based on the subject video clip, the saliency signal indicating where in the subject video clip a PPG signal is strongest.

3. The system of claim 1, wherein the training module further includes instructions that, when executed by the processor, cause the processor to warp the unlabeled video clip by passing the unlabeled video clip through a saliency sampler.

4. The system of claim 1, wherein the training module further includes instructions that, when executed by the processor, cause the processor to: generate anchor subset views based on the anchor PPG signal, negative subset views based on the negative PPG signal, and positive subset views based on the positive PPG signal, wherein the anchor subset views, negative subset views, and positive subset views have one or more views that correspond to each other; determine a positive total based on a distance between corresponding anchor subset views and positive subset views; determine a negative total based on a distance between corresponding anchor subset views and negative subset views; and determine a difference between the positive total and the negative total to generate the first loss.

5. The system of claim 1, wherein the training module further includes instructions that, when executed by the processor, cause the processor to adjust the one or more model weights of the remote PPG model based on a second loss using a second loss function that uses the anchor PPG signal and aground truth PPG signal.

6. The system of claim 5, wherein the second loss function includes at least one of a Pearson's correlation loss function, a signal-to-noise ratio loss function, and a maximum cross-correlation loss function.

7. The system of claim 6, wherein the training module further includes instructions that, when executed by the processor, cause the processor to
  subtract a means of the anchor PPG signal and the ground truth PPG signal from the anchor PPG signal and the ground truth PPG signal;
  determine a cross-correlation of the anchor PPG signal and the ground truth PPG signal by taking a fast Fourier transform of the anchor PPG signal and the ground truth PPG signal and multiplying one of the anchor PPG signal and the ground truth PPG signal with a conjugate of the other;
  filter the cross-correlation to remove cross-correlations outside a range of an expected heart rate to generate a filtered spectrum of cross-correlation;
  determine a final cross-correlation by taking an inverse of the fast Fourier transform of the filtered spectrum of cross-correlation and dividing by standard deviations of the anchor PPG signal and the ground truth PPG signal; and
  wherein a maximum of the final cross-correlation is the second loss.

8. A method for training a remote photoplethysmography ("PPG") model that outputs a subject PPG signal based on a subject video clip of a subject, the method comprising steps of training the remote PPG model in a self-supervised contrastive learning manner using an unlabeled video clip having a sequence of images of a face of a person;
  further the method comprising the steps of:
  resampling the unlabeled video clip at a first frequency ratio to generate a negative sample clip;
  passing the unlabeled video clip through the remote PPG model to generate an anchor PPG signal:
  passing the negative sample clip through the remote PPG model to generate a negative PPG signal;
  resampling the negative PPG signal at a second frequency ratio to generate a positive PPG signal, wherein the second frequency ratio is an inverse of the first frequency ratio and adjusting one or more model weights of the remote PPG model based on a first loss calculated using a first loss function that considers the anchor PPG signal, the negative PPG signal, and the positive PPG signal.

9. The method of claim 8, wherein the remote PPG model is configured to output a saliency signal based on the subject video clip, the saliency signal indicating where in the subject video clip a PPG signal is strongest.

10. The method of claim 8, further comprising the step of warping the unlabeled video clip by passing the unlabeled video clip through a saliency sampler.

11. The method of claim 8, further comprising the steps of:
  generating anchor subset views based on the anchor PPG signal, negative subset views based on the negative PPG signal, and positive subset views based on the positive PPG signal, wherein the anchor subset views, negative subset views, and positive subset views have one or more views that correspond to each other;
  determining a positive total based on a distance between corresponding anchor subset views and positive subset views;
  determining a negative total based on a distance between corresponding anchor subset views and negative subset views; and
  determining a difference between the positive total and the negative total to generate the first loss.

12. The method of claim 8, further comprising the step of adjusting the one or more model weights of the remote PPG model based on a second loss using a second loss function that uses the anchor PPG signal and a ground truth PPG signal.

13. The method of claim 12, wherein the second loss function includes at least one of a Pearson's correlation loss function, a signal-to-noise ratio loss function, and a maximum cross-correlation loss function.

14. The method of claim 13, further comprises the steps of:
  subtracting a means of the anchor PPG signal and the ground truth PPG signal from the anchor PPG signal and the ground truth PPG signal;
  determining a cross-correlation of the anchor PPG signal and the ground truth PPG signal by taking a fast Fourier transform of the anchor PPG signal and the ground truth PPG signal and multiplying one of the anchor PPG signal and the ground truth PPG signal with a conjugate of the other;
  filtering the cross-correlation to remove cross-correlations outside a range of an expected heart rate to generate a filtered spectrum of cross-correlation;
  determining a final cross-correlation by taking an inverse of the fast Fourier transform of the filtered spectrum of cross-correlation and dividing by standard deviations of the anchor PPG signal and the ground truth PPG signal; and
  wherein a maximum of the final cross-correlation is the second loss.

15. A non-transitory computer-readable medium having instructions that, when executed by a processor, cause the processor to train a remote photoplethysmography ("PPG") model in a self-supervised contrastive learning manner using an unlabeled video clip having a sequence of images of a face of a person, the remote PPG model is configured to output a subject PPG signal based on a subject video clip of a subject;
  wherein, when executed by the processor, cause the processor to:
  resample the unlabeled video clip at a first frequency ratio to generate a negative sample clip;
  pass the unlabeled video clip through the remote PPG model to generate an anchor PPG signal;
  pass the negative sample clip through the remote PPG model to generate a negative PPG signal;
  resample the negative PPG signal at a second frequency ratio to generate a Positive PPG signal, wherein the second frequency ratio is an inverse of the first frequency ratio; and
  adjust one or more model weights of the remote PPG model based on a first loss calculated using a first loss function that considers the anchor PPG signal, the negative PPG signal, and the positive PPG signal.

16. The non-transitory computer-readable medium of claim 15, wherein the remote PPG model is configured to output a saliency signal based on the subject video clip, the saliency signal indicating where in the subject video clip a PPG signal is strongest.

17. The non-transitory computer-readable medium of claim 15, further having instructions that, when executed by the processor, cause the processor to warp the unlabeled video clip by passing the unlabeled video clip through a saliency sampler.

* * * * *